United States Patent [19]

Masseron et al.

[11] Patent Number: Plant 7,714

[45] Date of Patent: Nov. 19, 1991

[54] APPLE ROOTSTOCK — LANCEP VARIETY

[75] Inventors: Alain Masseron, Castillon La Batille; Elisa Grillet, Lyons, both of France

[73] Assignees: Centre D'Experimentation de Pepinieres, Lyons; Centre Technique Interprofessionnel des Fruits et Legumes, Paris, both of France

[21] Appl. No.: 367,230

[22] Filed: Jun. 15, 1989

[51] Int. Cl.[5] ..... A01H 5/00

[52] U.S. Cl. ..... Plt./34

[58] Field of Search ..... Plt. 34–36

[56] References Cited

PUBLICATIONS

Childers, N. F., Chapter III, "Establishing the Fruit Planting", *Modern Fruit Science,* 4th Ed., 1969, Hort. Pubs. Rutgers Univ., pp. 44–53 relied on.

*Primary Examiner*—James R. Feyrer

*Attorney, Agent, or Firm*—Dennison, Meserole, Pollack & Scheiner

[57] ABSTRACT

The invention relates to a new and distinct virus-free variety of apple tree useful as a rootstock for supporting grafted apple varieties, particularly for planting of hedgerows of apple trees. The new variety originated as a clone of heat treated Paradis-Jaune-de-Metz selection, M9B, also called M9 INFEL. It has been found that there is better root lignification as well as generally several points of root issue on the clones as well as an increased vigor to the cultivars.

6 Drawing Sheets

The present invention relates to a new and distinct mutant of "M9" apple rootstock material, which has been treated and indexed to be virus-free rootstock apple tree Lancep which was selected from a test stool bed planting at the Lanxade Centre of the Centre Technique Interprofessionnal des Fruits et Legumes, Paris, France based on its outstanding rooting and dwarfing capacity differences.

In 1964, the English Paradis-Jaune-de-Metz selection, M9, was introduced in the Lanxade Centre. In 1968, during the development of heat treatment at the Centre, the M9 was one of the first clones to be regenerated by this technique. It was then called the M9 B and afterwards the M9 Infel.

In order to supply French nurserymen as soon as possible and enable fruit growers to dispose of virus-free M9, this clone was propagated by grafting, on apple tree seedlings, and prepropagated, by the grafted — earthed-up layering technique, in the Centre. During this prepropagation phase, 1970–1973, year after year, this selection was found to have a poor aptitude to root and issue shoots in stool beds. This phenomenon was certainly emphasized by the fact that the stock came from grafts on seedlings.

Several techniques were then tried in order to improve the production of layers: installation of bands in order to "compress" the twig at the onset of growth, planting by layering of stock, early and repeated earthing. Some of these techniques such as layered planting, gave better results. However, the production did not exceed 3 to 4 marketable plants per stock and difficulties were encountered during the mechanization of the harvest of layers.

It was therefore obvious that the M9 2 selection, as well as the original M9 a clone, presented difficulties in propagation. This defect is genetic. In 1974, in collaboration with the INRA and the profession, the multiplication of the M9 B was halted an a decision was made to set up a selection program among the Paradis-Jaune-de-Metz population found in France.

During 1974, several contacts were made with French propagators specializing in the production of rootstocks. In addition, visits were made to the main plots of Paradis-Jaune-de-Metz stool beds. During the following winter, 425 types were found and underwent experiments at Lanxade.

As of 1975, three series of studies were simultaneously carried out on these mutant plant materials:

Health control by indexing of the material introduced; The 5 lots were found to be infected with virus diseases, Spy Decline and CLS;

Establishing a trial on behavior during layering — Winter 1974–1975:

Trial A — Lanxade Centre, 30 stocks per clone, 2 repetations; and

Preparation of grafting in a nursery and trial on behavior in an orchard — Winter 1976–1977;

Trial B — Lanxade Centre — Balandran Centre, Valence Centre, 9 trees per clone, 2 repetitions.

In 1976, following the first observations of the test in a stool bed, Trial A, treatment by heat treatment was carried out on the original lots and 10 healthy clones, on the basis of 2 clones from each of the 5 lots, were obtained.

After rapid asexual propagation in a greenhouse and then outdoors, by grafting on seedlings, and new controls of the state of health by indexing, these 10 clones were compared in different trials beginning 1978, which trials comprised:

Trial on behavior during layering — Winter 1977–1978; Trial C — Lanxade, 30 stocks per clone, 2 repetitions;

Trial on behavior in a nursery of bench grafting in 1978 — Trial D — Lanxade, 60 plants per clone; and Trial on behavior in an orchard — Winter 1978–1979, Trial E — Lanxade-Balandran-Valence, 8 trees per clone, 2 repetitions.

After two years of observations in a stool bed, Trial C, 6 clones were selected in 1979 for their better aptitude to be propagated by layering: they are clones F, G, H, J, L and M. In 1981, after two additional years of study of the behavior during layering, Trial C, and after the initial results on the behavior in an orchard, Trial E, a selected mutant, namely Clone G, called Lancep, was retained.

Moreover, at the same time as these studies were carried out in France on the Paradis-Jaune-de-Metz, several creations were introduced at Lanxade for comparative purposes:

from England (East Malling Station) M9 A, in 1964, and M9 Emla, in 1975;
from Belgium, Gorsem Centre: 6 clones comprising the 2 selections KL 10 and KL 29, in 1974;
from the Netherlands, Wilhelminadorp Stations, T 337, T 338, T 339 and T 340, in 1976;
from Germany, Burgmer Nurseries in Straelen, SP 1, SP 2, SP 10 and SP 18, in 1977; and
from France, Inra Station in Versailles, regeneration by heat treatment of selections M9-3, M9-10, M9-31 bis and M9-35, work by Fleckinger, and selection of 8 clones numbered Lx 174 to Lx 181, in 1977.

As a rootstock, this mutation is virus-free and supports vigorous growth of the scion cultivar, making a "hedgerow" tree, and the scion cultivar shows a sharp increase, up to 30% in Valence Centre with trial of Golden×972 variety, in the total production after 7 years of most healthy clones as compared to the virus infected clone M9.

The following is a detailed description of the new cultivar Lancep. Accompanying photographs depict fruit characteristics, tree habit and leaf characteristics.

BRIEF DESCRIPTION OF THE DRAWINGS

The first photograph, FIG. 1, shows the fruit characteristics of the new variety. Short to medium length stems, fruit small, under 100 g., half-raised and irregular shape with a very narrow and shallow ocular cavity, a very closed eye, yellow green color with the presence of red on one cheek, a smooth and fairly waxy skin, and low acidity.

Asexual propagation of this new cultivar by layering as has been done at the Lanxade Centre, France, has shown that these attributes are transmitted through succeeding asexual propagations.

Figure 1:
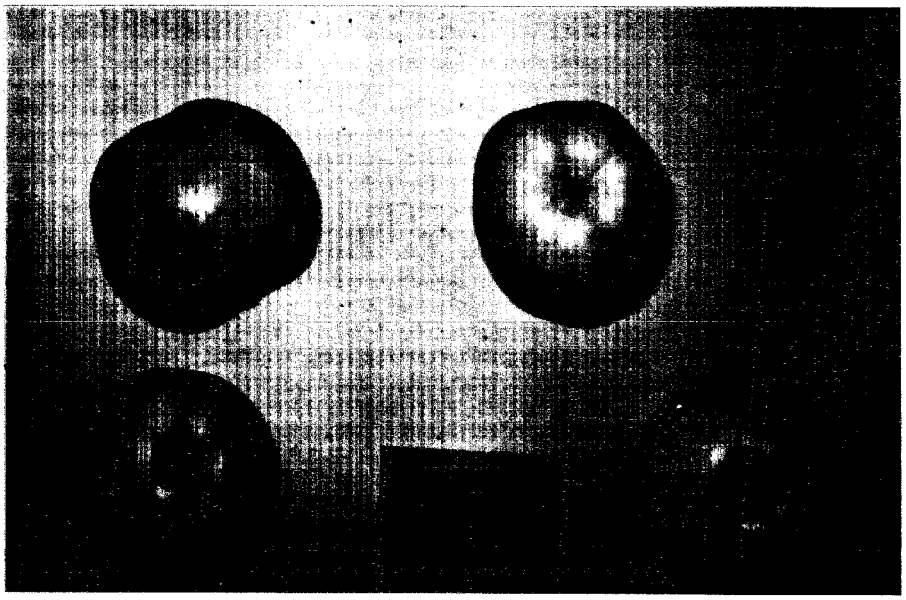
FIG. 1 shows the fruit of the new variety.
Figure 2A:
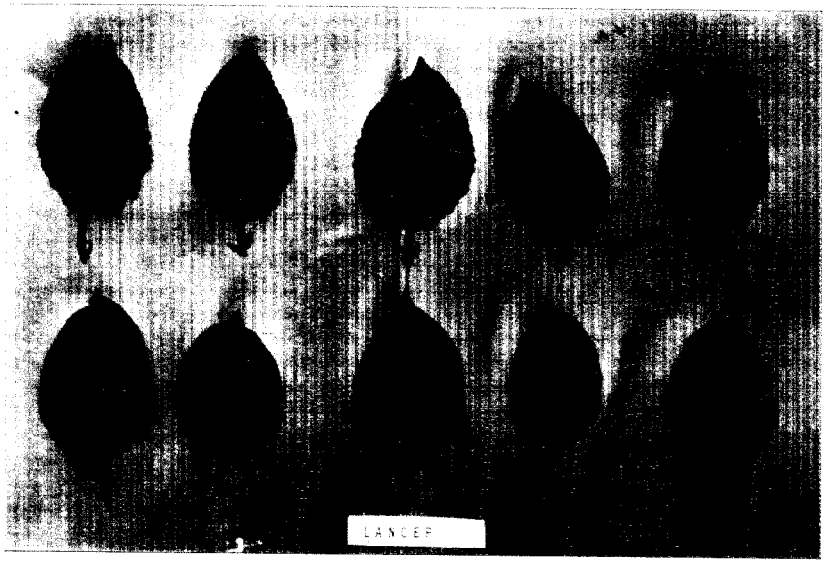
FIG. 2A shows the adaxial surfaces of the leaves of the new variety.
Figure 2B:
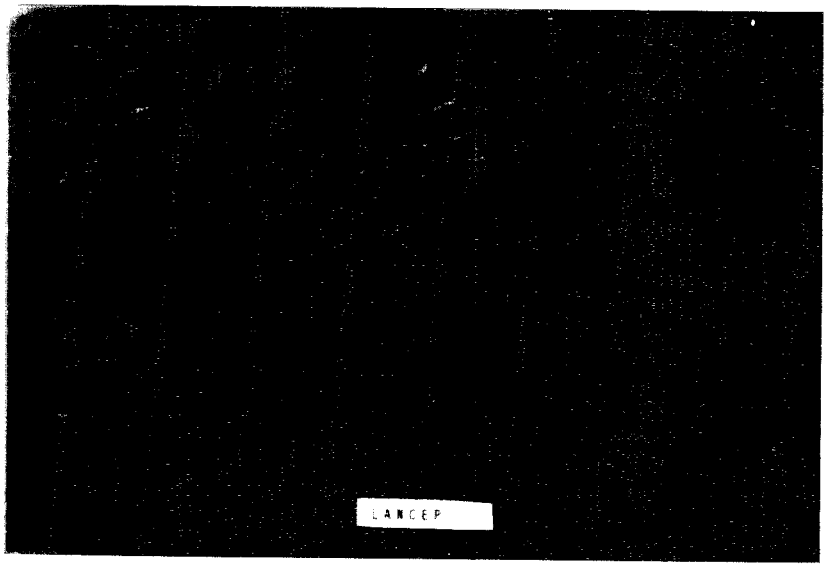
FIG. 2B shows the abaxial surfaces of the leaves of the new variety.

FIGS. 2A and 2B show respectively the adaxial and abaxial surfaces of the leaves of the new variety, of small size, having a length of lamina of about 85 mm and a width of lamina of about 56 mm and length of petiole of about 28.5 mm.

Figure 3B:
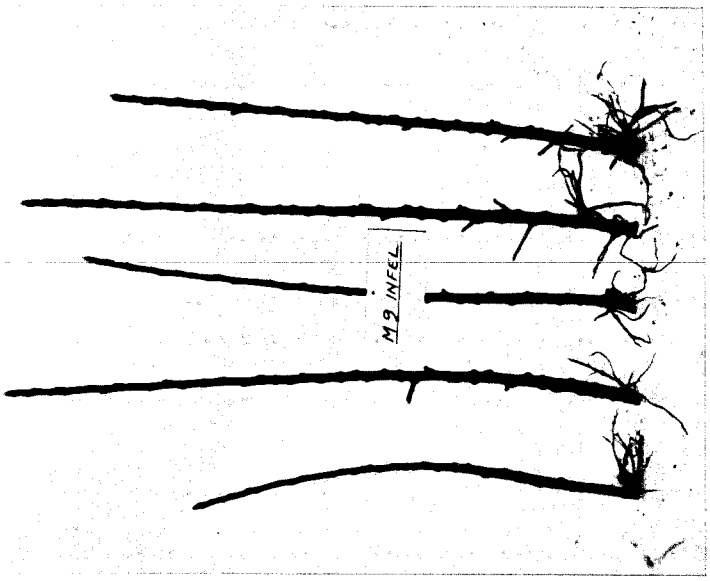
FIGS. 3A & 3B show the general appearance of the appearance of Lancep twigs as opposed to M9 twigs.
Figure 3A:
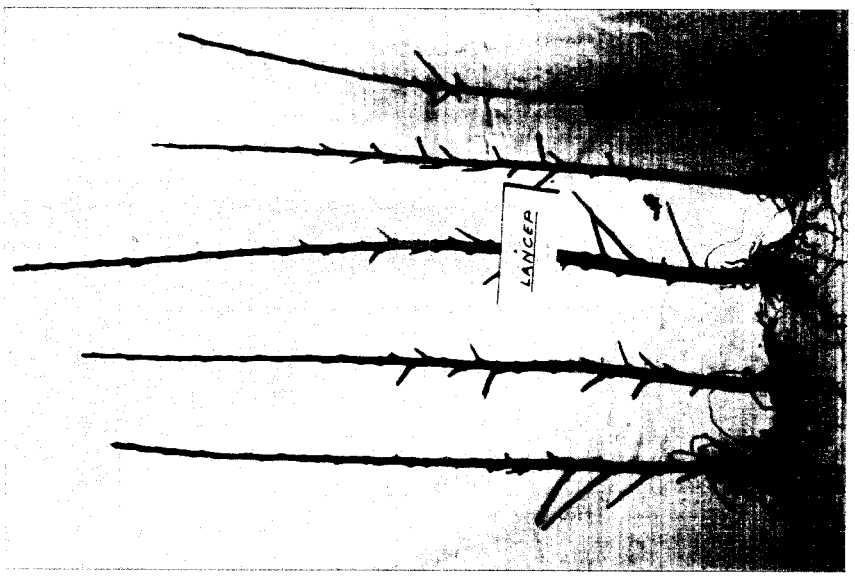

The third photograph, FIG. 3, shows the general appearance of Lancep twigs as opposed to M9 Infel twigs.

Figure 4:
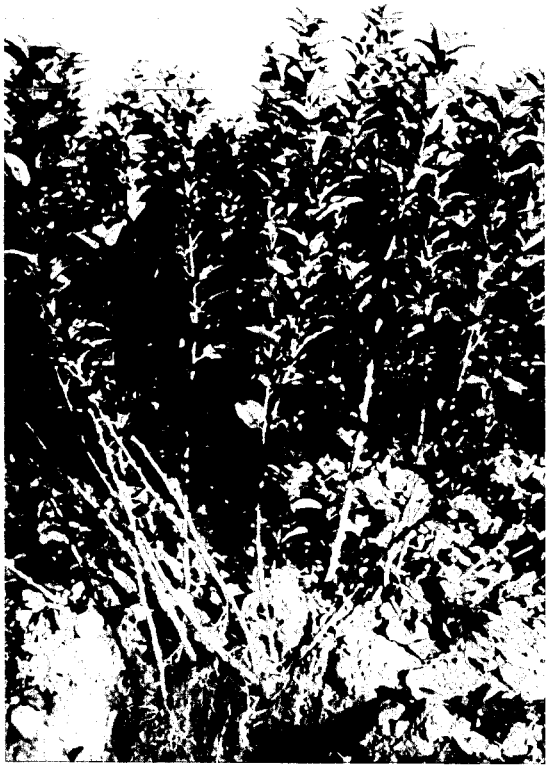
FIG. 4 shows Lancep rooting in stoolbeds.

The fourth photograph, FIG. 4, shows Lancep rooting in stool beds.

Figure 5:
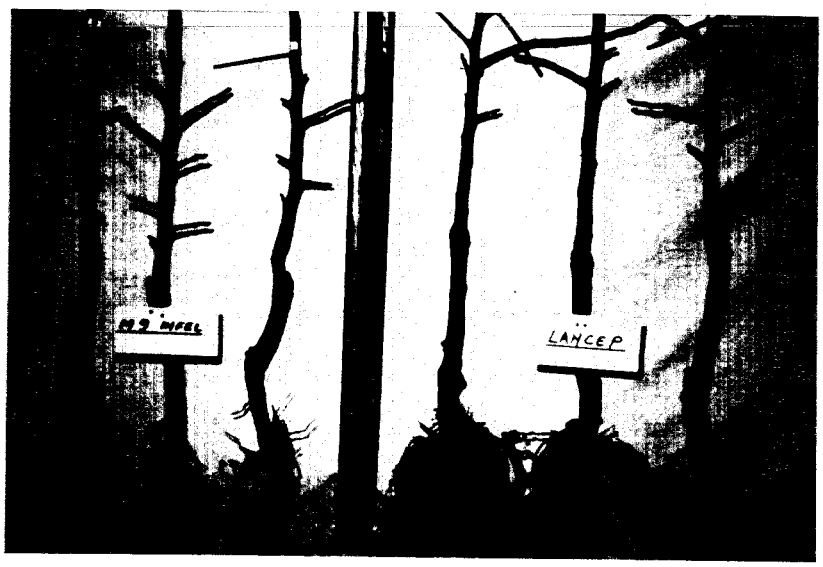
FIG. 5 shows the root system for scions of Golden×972 variety grated on Lancep.

The fifth photograph, FIG. 5, shows the root system for scions of Golden×972 variety grafted on Lancep by dormant bud grafting.

Figure 6:
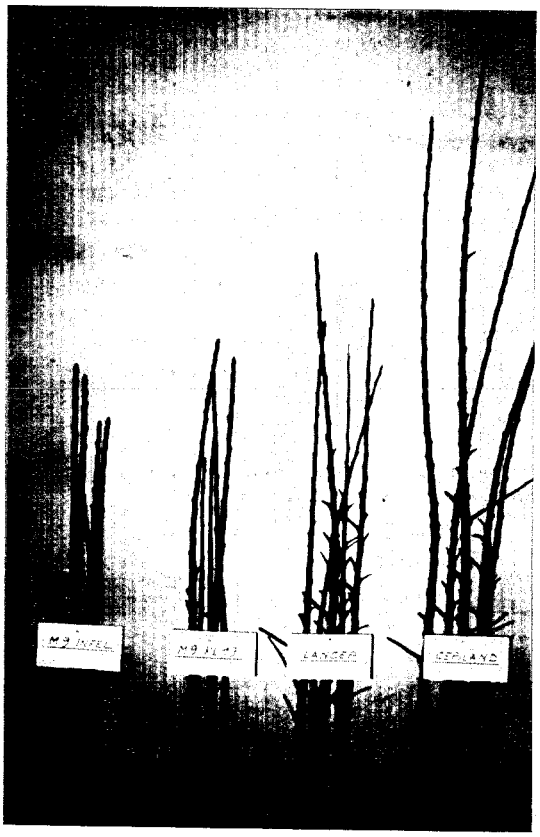
FIG. 6 shows layers of M9 Infel; M9 KL 19; and Lancep.

The sixth photograph, FIG. 6, shows layers of several Paradis Jaune-de-Metz selections at harvest, namely M9 Infel; KL 19, Lancep: and Cepiland.

Figure 7:
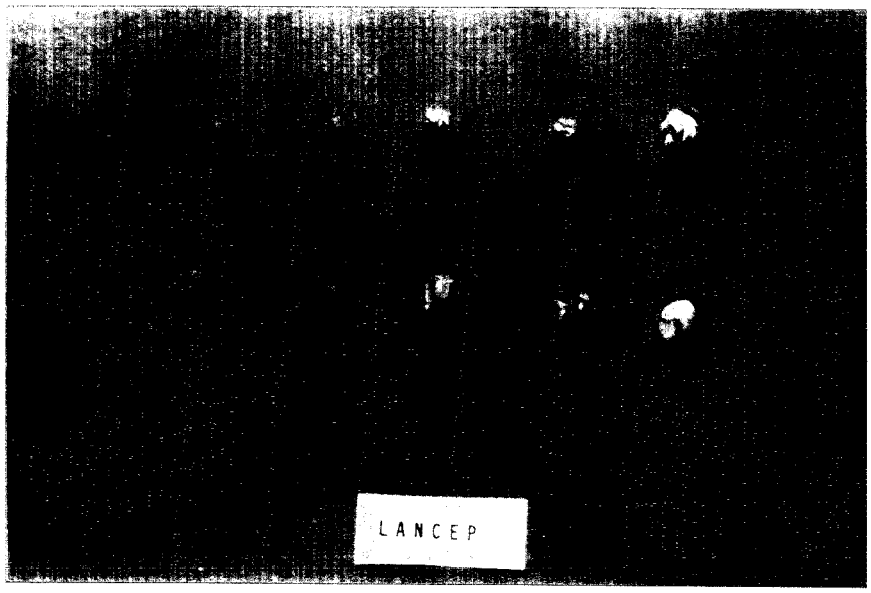
FIG. 7 shows unopened flowers of the new variety.

FIG. 7 shows two rows of flowers, which when viewed from left to right show progressive opening of the flowers of Lancep and the deep pink color of the unopened flower.

Figure 8:
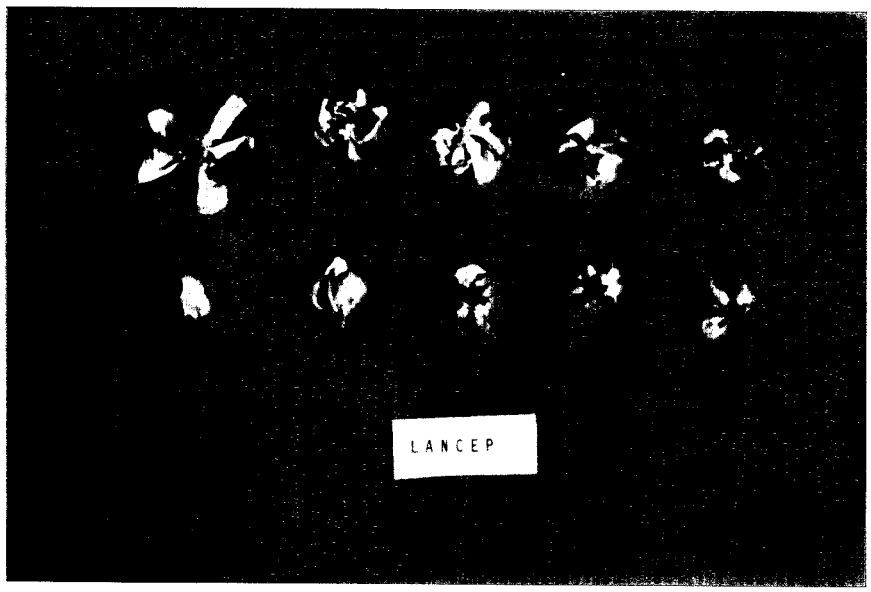
FIG. 8 shows fully open flowers of the new variety.

FIG. 8 shows two rows of flowers of Lancep and wherein viewed from left to right the two flowers in the lower row are progressively open more than in FIG. 7 and the remaining flowers in the lower row are viewed from the pedicel, and when so viewed still exhibit the deep pink color of the unopened flower and wherein the top row of open flowers will be seen to be characterized by a pinkish white color when viewed from the stamens and anthers.

The new variety is further characterized as follows:

FRUIT

Observations of the characteristics of the fruit of the new variety, based on a sample comprising 20 apples, gathered from an orchard comprising the new variety, without scion cultivars grafted thereon, were gathered in 1981. The sampled fruit have characteristics of early ripening, latter half of July, small size, e.g. under 100 g., with a half raised and irregular shape with a very narrow and shallow ocular cavity, a very closed eye, short to medium length stem, yellow-green color with the presence of red on one cheek, a smooth and fairly waxy skin and low acidity. These observations are similar to those mentioned in *A New Stock For Grafting Of Apple Trees: Paradis Jaune,* Review Horticole, 1879, pp 436–437.

TREE

Hedgerow tree which reaches its final volume in 4 to 5 years with a filiform twig and many feathers. The tree has an absence of known diseases, has an aptitude to propagation by layering superior to that of other virus-free clones currently available, 2 to 3 times marketable plants than M9 clones.

The agronomic behavior of the new variety in orchards is such that there is better homogeneity, since it is a clonal selection and no longer a population. The rootstock of the new variety has better compatibility with grafted varieties, with the grafted variety having 10 to 20% increased vigor and an increase in productivity of 10 to 30%.

LEAF AND TWIG CHARACTERISTICS

Physiological and morphological comparison tests have been carried out with a well known and characteristic type M9, the M9 Emla. The morphological differences in the leaves and twigs between Lancep and M9 Emla are indicated in Table 1.

TABLE 1

| | LEAF (Average) | | | |
|---|---|---|---|---|
| ROOTSTOCK | Length of lamina L (mm) | Width of lamina l (mm) | L + l (mm) | Length of petiole (mm) |
| M9 EMLA | 101.7 | 63.8 | 165.5 | 32.5 |
| LANCEP | 84.3 | 56.3 | 140.6 | 28.5 |

TABLE 1-continued

| ROOTSTOCK | TWIG (Average) Height (cm) | Diameter (mm) | Internode (mm) | % twigs with feathers or fruit spurs |
|---|---|---|---|---|
| M9 EMLA | 70 to 70 | 8.7 | 16.4 | 10 to 20% |
| LANCEP | 80 to 100 | 6.8 | 19.5 | 30 to 41% |

The physiological differences in nursery are shown in Tables 2 and 3.

Success in Hardwood Cutting

Data in respect of cuttings of 25 cm in length, the base of which were soaked in an IBA solution at 1000 ppm for one minute, then powdered with talc and captane and immediately put into place in mid-October are shown in Table 2.

TABLE 2

| ROOTSTOCK | PERCENTAGE OF ROOTING |
|---|---|
| M9 EMLA | 2% |
| LANCEP | 46% |

Aptitude for Stoolbed Layering

Table 3 shows the number of marketable layers per strain of the new variety Lancep vis-a-vis M9 of which it is a mutant.

TABLE 3

| ROOTSTOCK | From the 2nd to the 4th years (annual average/3 years) | From the 5th to the 11th years (annual average/7 years) |
|---|---|---|
| M9 EMLA | 1,4 | 6 |
| LANCEP | 5.8 | 16.5 |

TWIG

There is a high correlation between the size of the leaf and the twig characteristics, i.e., clone with small leaves has a filiform twig with many feathers and is tall. The clone of the new variety has a filiform twig with very feathers and results in a tall twig. The average twig of the new variety has a height of about 80 to 100 cm, a diameter of about 6.8 mm, an internode distance of about 19.5 mm, and the percentage of twigs with feathers or fruit spurs is about 30 to 40% of plants over 5 years old.

LEAVES

Measurement of the size of the lamina and the petiole, on 50 leaves collected in August, between the 5th and 10th merithal from the end of the new twig growth, for 2 years, that is, 100 leaves per clone, was statistically interpreted as the sum L+1, i.e., length+width, of the lamina. The average length of lamina "L" of the average leaf is about 84.3 mm and the average width of lamina about 56.3 mm. The leaf L+1 average of the new variety was thus formed to be about 140.6 mm, and the average length of petiole about 28.5 mm. The leaf is of a small general appearance.

COMPARISON OF NEW VARIETY LANCEP AND M9 EMLA

LANCEP

Brief description:
- *Vigor.*—Average.
- *Habit.*—Semi-spreading.
- *Appearance of branching.*—Filiform.
- *Internodes.*—Fairly long.
- *Expectation.*—Fairly fruitful in the early years.
- *Leaf.*—Average.
- *Roots.*—Brittle.
- *Change.*—Fairly sensitive to draught.

Behavior in orchard:
- *Compatibility.*—Fairly good (presence of a graft ridge).
- *Level of vigor.*—Week (+10 to +20% of ordinary M9).
- *Setting of fruit.*—Very good.
- *Productivity.*—Good, isometric (+15 to +30% of ordinary M9).
- *Characteristics of the fruit.*—Good caliber, improved color and early maturity.
- *Anchoring.*—Weak (staking necessary).
- *Adaptation to sun.*—Average (in fertile healthy soil).

Multiplication capability:
- *Layering.*—Good.
- *Propagation of cuttings.*—Average.
- *Micropropagation.*—Average.
- *Behavior in the grafting nursery.*—Fairly good.

Sensitivities:
- *Gnarls.*—Slight to average sensitivity.
- *Shoots.*—Average sensitivity.
- *Root suffocation.*—Average sensitivity.
- *Limestone.*—Slight to average sensitivity.
- *Winter cold.*—Sensitive.
- *Phytophthora.*—Slightly sensitive.
- *Root rot.*—Average sensitivity to sensitive.
- *Crown gall.*—Sensitive.
- *Fire blight bacteria.*—Average sensitivity to sensitive.
- *Virus.*—Slightly sensitive.
- *Wooly aphis.*—Sensitive.
- *Fungi.*—Sensitive.
- *Rabbits.*—Sensitive.

M9 EMLA

Brief description:
- *Vigor.*—Weak.
- *Habit.*—Semi-erect.
- *Appearance of branching.*—Fairly stocky.
- *Internodes.*—Average to fairly short.
- *Expectation.*—Few number of fruit.
- *Leaf.*—Large.
- *Roots.*—Brittle.
- *Change.*—Fairly sensitive to draught.

Behavior in orchard:
- *Compatibility.*—Fairly good (presence of a graft ridge).
- *Level of vigor.*—Average (+15 to +30% of ordinary M9).
- *Setting of fruit.*—Very good.
- *Productivity.*—Good, isometric (+15 to +30% of ordinary M9).
- *Characteristics of the fruit.*—Good caliber, improved color and early maturity.

*Anchoring.*—Weak (staking necessary).
*Adaptation to sun.*—Average (in fertile healthy soil).

Multiplication capability:
*Layering.*—Average.
*Propagation of cuttings.*—Weak.
*Micropropagation.*—Mediocre.
*Behavior in the grafting nursery.*—Fairly good.

Sensitivities:
*Gnarls.*—Slightly sensitive.
*Shoots.*—Slight sensitivity.
*Root suffocation.*—Average sensitivity.
*Limestone.*—Slight to average sensitivity.
*Winter cold.*—Sensitive.
*Phytophthora.*—Slightly sensitive.
*Root rot.*—Average sensitivity to sensitive.

*Crown gall.*—Sensitive.
*Fire blight bacteria.*—Average sensitivity to sensitive.
*Virus.*—Slightly sensitive.
*Wooly aphis.*—Sensitive.
*Fungi.*—Sensitive.
*Rabbits.*—Sensitive.

We claim:

1. A new and distinct virus-free variety of apple tree useful as an improved rootstock for apple cultivars, substantially as illustrated and described, which when used as such rootstock has better compatibility with all commercial varieties, facilitates more vigorous growth and increases productivity of the grafted variety.

* * * * *